US010357517B1

(12) United States Patent
Borlongan et al.

(10) Patent No.: US 10,357,517 B1
(45) Date of Patent: Jul. 23, 2019

(54) METHODS OF TREATING EPILEPSY USING NEURAL STEM CELLS THAT EXPRESS NANOG, SSEA-4, OCT-4, MIR-34B, MIR-34C AND MIR-592

(71) Applicants: Cesario Venturina Borlongan, Tampa, FL (US); Carmelina Gemma, Bellevue, WA (US); Fernando L. Vale, Tampa, FL (US)

(72) Inventors: Cesario Venturina Borlongan, Tampa, FL (US); Carmelina Gemma, Bellevue, WA (US); Fernando L. Vale, Tampa, FL (US)

(73) Assignees: University of South Florida, Tampa, FL (US); The United States of America as Represented by the Department of Veterans Affairs, Washington, DC (US); Office of General Counsel—PSG IV (024), Washington, DC (US)

( * ) Notice: Subject to any disclaimer, the term of this patent is extended or adjusted under 35 U.S.C. 154(b) by 68 days.

(21) Appl. No.: 14/974,088

(22) Filed: Dec. 18, 2015

Related U.S. Application Data

(62) Division of application No. 14/043,221, filed on Oct. 1, 2013, now abandoned.

(60) Provisional application No. 61/708,244, filed on Oct. 1, 2012.

(51) Int. Cl.
A61K 48/00 (2006.01)
A01N 63/00 (2006.01)
C12N 5/00 (2006.01)
C12N 5/079 (2010.01)
C12N 5/0797 (2010.01)
C12N 5/0793 (2010.01)
C12N 5/074 (2010.01)
C12N 5/0735 (2010.01)
C12N 5/071 (2010.01)
C12N 5/07 (2010.01)
C12N 5/16 (2006.01)
A61K 35/30 (2015.01)
A61K 9/00 (2006.01)
G01N 33/50 (2006.01)
C12Q 1/6809 (2018.01)
C07K 14/435 (2006.01)

(52) U.S. Cl.
CPC ............ A61K 35/30 (2013.01); A61K 9/0085 (2013.01); A01K 2267/025 (2013.01); C07K 14/435 (2013.01); C12N 5/00 (2013.01); C12N 5/06 (2013.01); C12N 2501/603 (2013.01); C12N 2501/605 (2013.01); C12N 2506/08 (2013.01); C12Q 1/6809 (2013.01); G01N 33/5058 (2013.01); G01N 33/5073 (2013.01)

(58) Field of Classification Search
CPC .......................... C12N 5/0606; C12N 5/0696; C12N 2506/02; C12N 5/0623; C12N 5/0619; C12N 2506/45; C12N 5/0607; C12N 5/0618; C12N 2501/603; C12N 15/85; C12N 5/0622; C12N 2500/84; C12N 2501/605; C12N 5/0692; A61K 35/30; A61K 35/12; A61K 2300/00; A61K 35/28; A61K 35/545; A61K 9/0085; A61K 38/17; A61K 2039/515; C07K 14/435; C07K 14/47; G01N 33/5044; G01N 33/5058; G01N 2500/10; G01N 2800/28; G01N 33/5073; G01N 33/6896; G01N 33/56966; A01K 2267/025; A61P 25/28; C12Q 1/6809
See application file for complete search history.

(56) References Cited

U.S. PATENT DOCUMENTS

| | | | |
|---|---|---|---|
| 5,968,829 A | 10/1999 | Carpenter | |
| 6,497,872 B1 | 12/2002 | Weiss et al. | |
| 6,787,355 B1 | 9/2004 | Miller et al. | |
| 7,166,277 B1 | 1/2007 | Weiss et al. | |
| 7,531,354 B2* | 5/2009 | Stice | C12N 5/0619 435/325 |
| 7,601,495 B2* | 10/2009 | Chen | C12Q 1/686 435/6.12 |
| 7,691,629 B2 | 4/2010 | Johe et al. | |
| 7,709,616 B2* | 5/2010 | Bentwich | C12N 15/111 435/375 |
| 8,067,233 B2* | 11/2011 | Totey | C12N 5/0607 435/325 |
| 8,178,089 B2* | 5/2012 | Stice | C12N 5/0619 424/93.7 |
| 8,367,406 B2* | 2/2013 | Kopyov | A01N 1/0205 435/325 |
| 8,442,772 B2* | 5/2013 | Loring | G06F 19/24 424/93.1 |
| 9,220,729 B2* | 12/2015 | Kriegstein | A61K 35/30 |
| 2005/0272149 A1* | 12/2005 | Brustle | A01K 67/0271 435/368 |

(Continued)

OTHER PUBLICATIONS

Girard et al., Nature 2006; 442: 199-202.*

(Continued)

Primary Examiner — Chang-Yu Wang
(74) Attorney, Agent, or Firm — Thomas|Horstemeyer, LLP

(57) ABSTRACT

Provided herein is a method of diagnosing or prognosing an epilepsy or epilepsy-related disorder. Also provided herein is a method of treating an epilepsy or epilepsy-related disorder. Further provided are non-epileptic and epileptic neural stem cells and cell cultures.

14 Claims, 16 Drawing Sheets
Specification includes a Sequence Listing.

(56) References Cited

U.S. PATENT DOCUMENTS

| | | | | |
|---|---|---|---|---|
| 2006/0073587 | A1* | 4/2006 | Stice | C12N 5/0619 435/325 |
| 2009/0136456 | A1* | 5/2009 | Huang | C12N 5/0623 424/93.7 |
| 2009/0263360 | A1* | 10/2009 | Stice | C12N 5/0619 424/93.7 |
| 2010/0055079 | A1 | 3/2010 | Sekula, Jr. | |
| 2010/0080780 | A1* | 4/2010 | Pitaru | C12N 5/0632 424/93.7 |
| 2010/0233804 | A1* | 9/2010 | Zhou | C12N 5/0696 435/354 |
| 2010/0297087 | A1* | 11/2010 | Seligman | C12N 5/0611 424/93.7 |
| 2011/0118130 | A1* | 5/2011 | Loring | G06F 19/24 506/7 |
| 2011/0165129 | A1* | 7/2011 | Kriegstein | A61K 35/30 424/93.7 |
| 2012/0207723 | A1* | 8/2012 | He | A61K 35/12 424/93.21 |
| 2013/0202568 | A1* | 8/2013 | Kriegstein | A61K 35/30 424/93.7 |
| 2014/0141986 | A1* | 5/2014 | Spetzler | C12Q 1/6886 506/9 |
| 2014/0234263 | A1* | 8/2014 | Shiels | A61K 35/22 424/93.7 |

OTHER PUBLICATIONS

Bentwich, Nat. Genet. 2005; 37:766-770.*
Proc. Natl. Acad. Sci. U.S.A. 2002; 99:16899-16903.*
Jung et al. Epilepsia 2009, 50:537-549.*
Shindo et al. Neurol. Med. Chir 2010, 50:98-106.*
Shetty et al. Stem cells; 2007; 25:2396-407.*
Shetty et al. Neurosci. Biobehav. Rev. 2016; 62:35-47.*
Peng et al. Am. J. Pathol., 2018; 188: 23-28.*
Zhang et al. Curr. Mol. Med. 2013; 13:1432-1445.*
Thodeson et al. Cell Tissue Res. 2018; 371:47-54.*
Pai et al. Front. Cell. Neurosci. Jan. 13, 2014;doi:103389/fncel.2013.00285.*
Hunt Interneuron transplantation as a treatment for epilepsy; Additional Perspectives on Epilepsy: The Biology of Spectrum Disorder 2015, Coldoi:1101/cspperspect.a022376.*
Liu et al., The microRNA miR-34 modulates ageing and neurodegeneration in *Drosophila*. Nature 482:7386, Feb. 2012 pp. 519-523 and corresponding methods pages (unnumbered).
Zovoilis et al., microRNA-34c is a novel target to treat dementias, EMBO Journal 30:20, 2011, pp. 4299-4308.
Naegele et al., Gene and stem cell therapies for treating epilepsy, 2010.
Aranha et al., miR-34a regulates mouse neural stem cell differentiation. PloS one 6:8, 2011, pp. e21396.
De Smaele et al., MicroRNAs as biomarkers for CNS cancer and other disorders, Brain research 1338, Jun. 18, 2010, pp. 100-111.
Aronica et al., Expression pattern of miR-146a, an inflammation-associated microRNA, in experimental and human temporal lobe epilepsy, European Journal of Neuroscience 31:6, 2010, 1100-1107.
Ayuso-Sacido et al., Long-term expansion of adult human brain subventricular zone precursors, Neurosurgery 62:1, 2008, pp. 223-231.
Haramati et al., MicroRNA as repressors of stress-induced anxiety: the case of amygdalar miR-34, J Neurosci 31:40, 2011, pp. 14191-14203.
Azevedo-Pereira et al., Isolation of neurosphere-like bodies from an adult patient with refractory temporal lobe epilepsy, Arquivos de neuro-psiquiatria 68:6, 2010, pp. 956-958.
Gaughwin, Hsa-miR-34b is a plasma-stable microRNA that is elevated in pre-manifest Huntington's disease, Human Molec. Genet., 20:11, 2011, pp. 2225-2237.

Oberg et al., miRNA Expression in Colon Polyps Provides Evidence for a Multihit Model of Colon Cancer, PLoS One, 6:6, 2011, pp. 1-12.
Genovesi et al., Integrated Analysis of miRNA and mRNA Expression in Childhood Medulloblastoma Compared with Neural Stem Cells, PLoS One, 6:9, 2011, pp. 1-12.
Berezikov et al., Approaches to MicroRNA discovery, Nat. Genetics, 38, 2006, pp. S2-S7.
Rao et al., Hippocampal neurodegeneration, spontaneous seizures, and mossy fiber sprouting in the F344 rat model of temporal lobe epilepsy, J. Neurosci Res., May 1, 2006, 83:6; pp. 1088-1105.
Ashhab et al., Expressions of Tumor Necrosis Factor Alpha and MicroRNA-155 in Immature Rat Model of Status Epilepticus and Children with Mesial Temporal Lobe Epilepsy, J. Mol. Neurosci, May 1, 2013.
Liu et al., MicroRNA-based therapy: a new dimension in epilepsy treatment, Int. J. Neurosci, May 9, 2013.
Sun et al., A Transient Upregulation of Glutamine Synthetase in the Dentate Gyrus is Involved in Epileptogenesis Induced by Amygdala Kindling in the Rat, PLoS One, 8:6, Jun. 18, 2013.
Bakir-Gungor et al., Identifying SNP targeted pathways in partial epilepsies with genome-wide association study data, Epilepsy Res., 105:1-2, 2013, pp. 92-102.
Jimenez-Mateos et al., Epilepsy and microRNA, Neurosci, 238, May 15, 2013, pp. 218-229.
Ilhan-Mutlu et al., Comparison of microRNA expression levels between initial and recurrent glioblastoma specimens, J. Neurooncol, 112:3, May 2013, pp. 347-354.
Peng et al., Expression patterns of miR-124, miR-134, miR-132, and miR-21 in an immature rat model and children with mesial temporal lobe epilepsy, J. Mol. Neurosci., 50:2, Jun. 2013, pp. 291-297.
Risbud et al., Changes in microRNA expression in the whole hippocampus and hippocampal synaptoneurosome fraction following pilocarpine induced status epilepticus, PLoS One, 8:1, 2013.
Manna et al., A Relationship between genetic variant in pre-microRNA-146a and genetic predisposition to temporal lobe epilepsy: a case-control study, Gene, 516:1, Mar. 1, 2013, pp. 181-183.
Hu et al., MicroRNA expression profile of the hippocampus in a rat model of temporal lobe epilepsy and miR-34a-targeted neuroprotection against hippocampal neurone cell apoptosis post-status epilepticus. BMC Neurosci. 13:115, Sep. 22, 2012.
Iyer et al., MicroRNA-146a: a key regulator of astrocyte-mediated inflammatory response, PLoS One 7:9, 2012.
You et al., Significance of miR-196b in tumor-related epilepsy of patients with gliomas, PLoS One 7:9, 2012.
Nakajima et al., Molecular motor KIF5A is essential for GABA(A) receptor transport, and KIF5A deletion causes epilepsy, Neuron 76:5, Dec 6, 2012, pp. 945-961.
Singh et al., Lafora disease E3 ubiquitin ligase matin is recruited to the processing bodies and regulates the microRNA-mediated gene silencing process via the decapping enzyme Dcp1a, RNA Biol 9:12, Dec. 1, 2012, pp. 1440-1449.
Rowles et al., FTO, RNA epigenetics and epilepsy, Epigenetics 7:10, Oct. 2012, pp. 1094-1097.
Omran et al., MicroRNAs: a light into the "black box" of neuropediatric diseases? Neuromolecular Med. 14:4, Dec. 2012, pp. 244-261.
McKiernan et al., Expression profiling the microRNA response to epileptic preconditioning identifies miR-184 as a modulator of seizure-induced neuronal death, Exp Neurol 237:2, Oct. 2012, pp. 346-354.
Hsu et al., Loss of microRNAs in pyramidal neurons leads to specific changes in inhibitory synaptic transmission in the prefrontal cortex, Mol Cell Neurosci. 50:3-4, Jul. 2012, pp. 283-292.
Omran et al., Interleukin-1β and microRNA-146a in an immature rat model and children with mesial temporal lobe epilepsy, Epilepsia 53:7, Jul. 2012, pp. 1215-1224.
Jimenez-Mateos et al., Silencing microRNA-134 produces neuroprotective and prolonged seizure-suppressive effects, Nat Med 18:7, Jul. 2012, pp. 1087-1094.
McKiernan et al., Reduced mature microRNA levels in association with dicer loss in human temporal lobe epilepsy with hippocampal sclerosis, PLoS One, 7:5, 2012.

(56) References Cited

OTHER PUBLICATIONS

Kan et al., Genome-wide microRNA profiling of human temporal lobe epilepsy identifies modulators of the immune response, Cell Mol Life Sci. 69:18, Sep. 2012, pp. 3127-3145.

Sano et al., MicroRNA-34a upregulation during seizure-induced neuronal death, Cell Death Dis., Mar. 22, 2012.

Pichardo-Casas I et al., Expression profiling of synaptic microRNAs from the adult rat brain identifies regional differences and seizure-induced dynamic modulation, Brain Res. 1436, Feb. 3, 2012, pp. 20-33.

Dobrossy et al., Neurorehabilitation with neural transplantation, Neurorehabil Neural Repair 24:8, Oct. 2010, pp. 692-701.

Bian et al., Functions of Noncoding RNAs in Neural Development and Neurological Diseases, Mol Neurobiol 44, 2011, pp. 359-373.

Lau et al., Dysregulated microRNAs in neurodegenerative disorders, Seminars in Cell & Developmental Biology, Sep. 2010, vol. 21 issue 7 pp. 768-773.

Minones-Moyano et al., MicroRNA profiling of Parkinson's disease brains identifies early downregulation of miR-34b/c which modulate mitochondrial function. Hum. Mol. Genet. Aug. 1, 2011;20(15):3067-78.

Li et al., microRNAs as novel regulators of stem cell pluripotency and somatic cell reprogramming, Bioessays 34:8, 2012, pp. 670-680.

Public Abstract, State stem cell agency application TR1-01200 Development of Cell Therapy for Epilepsy, California Institute for Regenerative Medicine, 2009.

* cited by examiner

| Customer ID | | 9101 | 9201 | 9601 | 9102 | 9202 | 9602 | 9103 | 9203 | 9603 |
|---|---|---|---|---|---|---|---|---|---|---|
| Group ID | | neocortex | | | hippocampus | | | amygdala | | |
| | | CEI7053001 | CEI7053004 | CEI7053007 | CEI7053002 | CEI7053005 | CEI7053008 | CEI7053003 | CEI7053006 | CEI7053009 |

| | miRNA | P | FDR | hippocampus vs neocortex | amygdala vs neocortex | amygdala vs hippocampus | | | | | | | | |
|---|---|---|---|---|---|---|---|---|---|---|---|---|---|---|
| RT PCR Result | miR-34b | 8.00E-05 | 4.10E-04 | 2.13 | 9.99 | 4.69 | 30.14 | 28.90 | 29.30 | 28.52 | 27.58 | 28.98 | 25.66 | 26.20 | 26.52 |
| | miR-34b* | 3.72E-02 | 4.64E-02 | 1.08 | 2.61 | 2.41 | 40.00 | 40.00 | 40.00 | 40.00 | 39.65 | 40.00 | 38.76 | 38.35 | 38.75 |
| | miR-34c | 1.43E-03 | 3.58E-03 | 4.67 | 20.87 | 4.47 | 37.14 | 33.28 | 35.06 | 33.13 | 30.78 | 34.91 | 29.15 | 30.51 | 32.67 |
| | miR-592 | 3.80E-03 | 6.33E-03 | 0.99 | 0.57 | 0.57 | 32.04 | 32.73 | 31.53 | 34.93 | 33.73 | 32.90 | 35.35 | 33.48 | 35.13 |
| | miR-1260b | 5.46E-01 | 5.46E-01 | 1.15 | 0.66 | 0.57 | 32.97 | 32.04 | 30.07 | 30.62 | 32.15 | 31.71 | 32.70 | 33.08 | 31.10 |
| miRNA Array Result | miR-34b | 3.00E-05 | 1.70E-03 | 2.00 | 4.26 | 2.12 | 5.48 | 5.99 | 5.35 | 6.41 | 7.19 | 6.23 | 8.57 | 7.33 | 7.19 |
| | miR-34b* | 0.00E+00 | 0.00E+00 | 2.61 | 11.32 | 4.34 | 8.78 | 9.11 | 9.36 | 10.42 | 11.27 | 9.72 | 13.08 | 12.48 | 12.19 |
| | miR-34c | 0.00E+00 | 0.00E+00 | 3.57 | 16.64 | 4.66 | 7.66 | 8.38 | 8.56 | 9.94 | 11.02 | 9.16 | 12.96 | 12.03 | 11.77 |
| | miR-592 | 3.00E-05 | 1.70E-03 | 0.91 | 0.91 | 0.99 | 9.98 | 9.67 | 9.91 | 8.63 | 8.68 | 8.38 | 8.66 | 8.31 | 8.69 |
| | miR-1260b | 1.00E-04 | 4.83E-03 | 0.66 | 0.96 | 0.91 | 12.03 | 11.77 | 11.51 | 10.91 | 10.45 | 10.58 | 10.16 | 10.55 | 10.82 |

Fold Changes
Data display here is raw CT values
P or FDR <0.01
P or FDR <0.05
Fold Changes Up >2

FIG. 2

Day 1

Day 1

Day 4

Day 4

Day 7

Day 7

Day 1

Day 1

Day 4

Day 4

Day 7

Day 7

Day 1

Day 1

Day 4

Day 4

Day 7

Day 7

Lesion Area

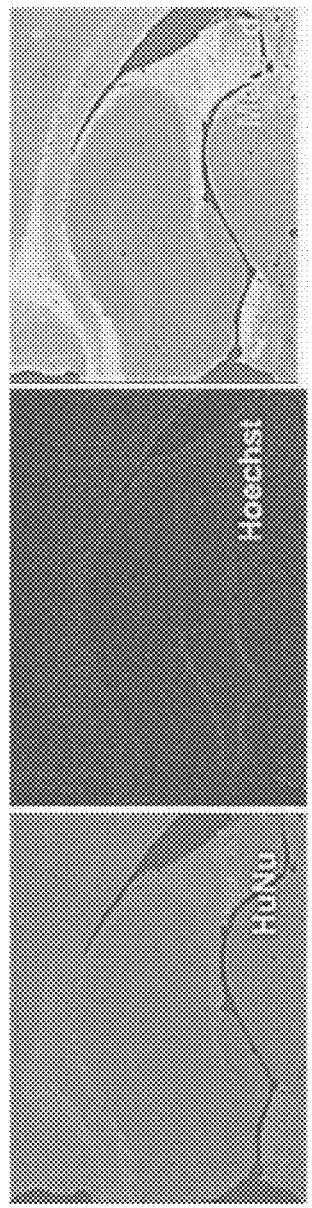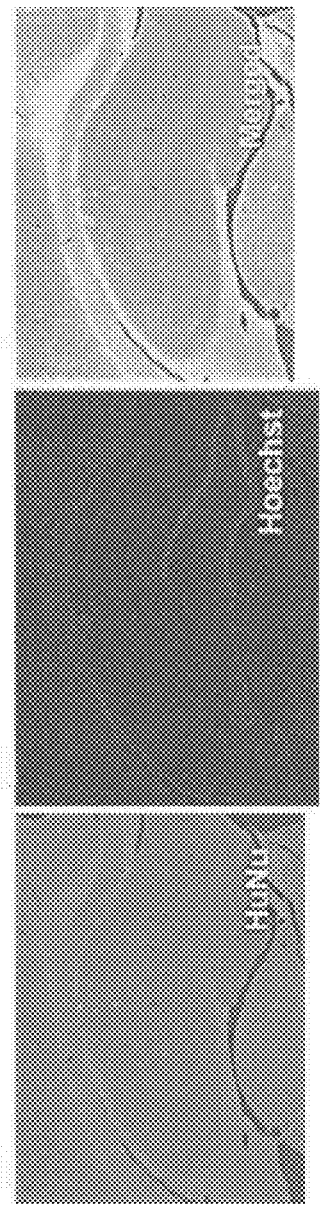

FIG. 12A  FIG. 12B  FIG. 12C
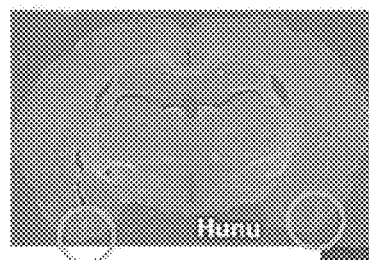
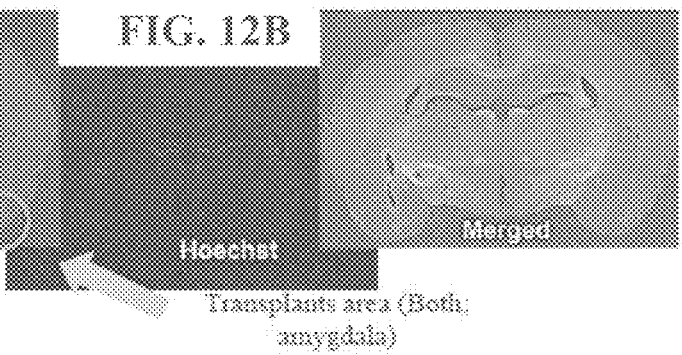
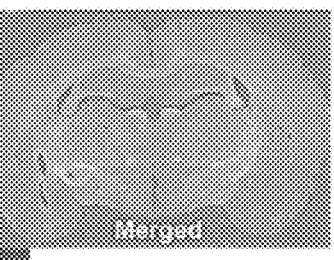
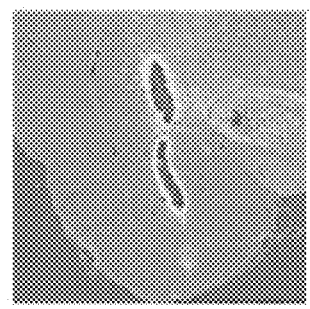
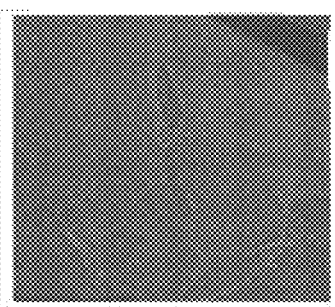
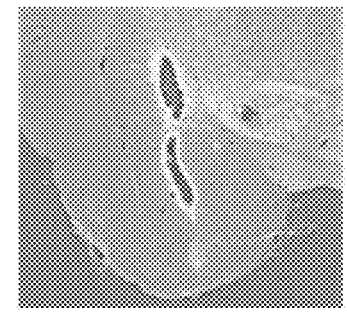
FIG. 12D  FIG. 12E  FIG. 12F
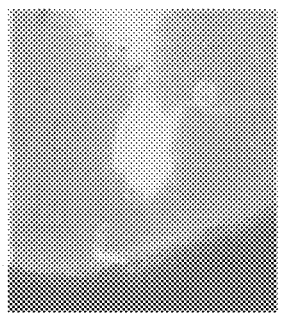
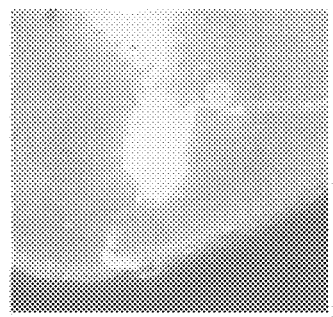
FIG. 12G  FIG. 12H

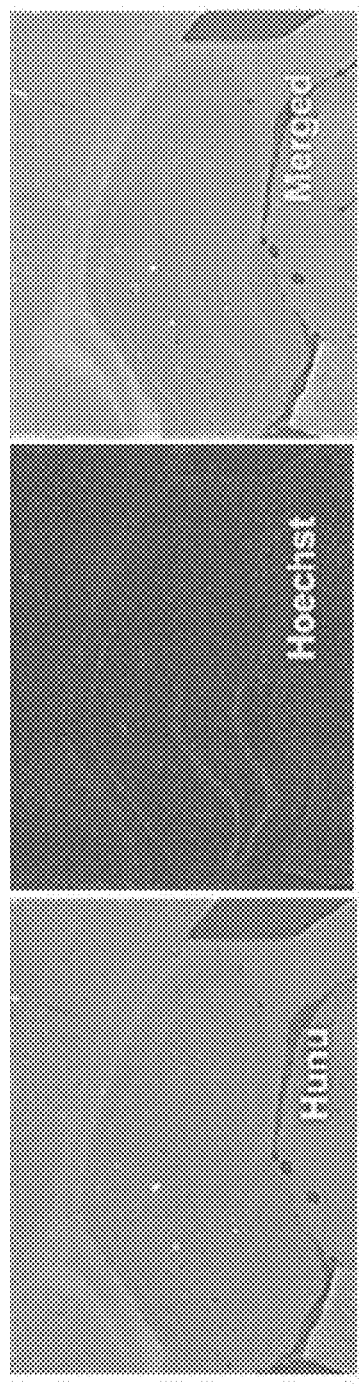
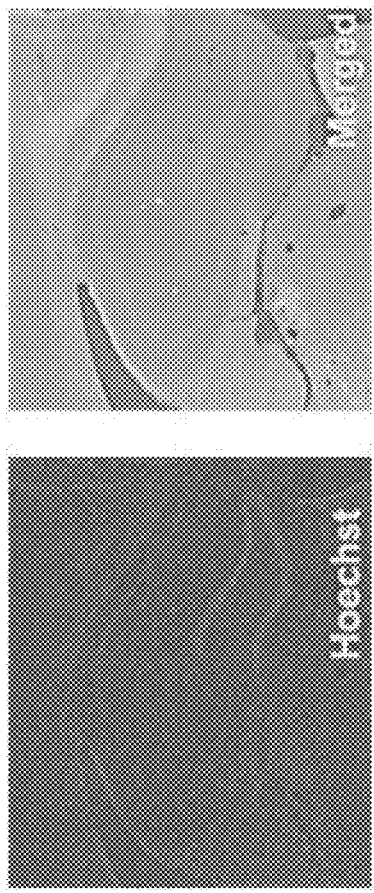
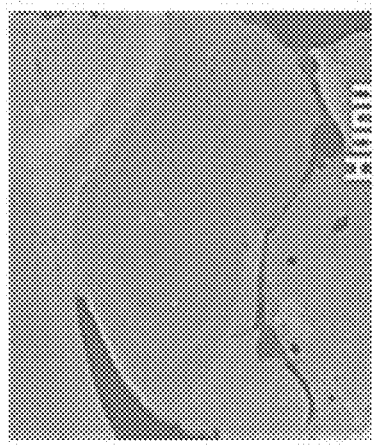

SEQUENCE LISTING

```
<160> NUMBER OF SEQ ID NOS: 4

<210> SEQ ID NO 1
<211> LENGTH: 23
<212> TYPE: RNA
<213> ORGANISM: Artificial Sequence
<220> FEATURE:
<223> OTHER INFORMATION: Mature sequence for miR-34b* (hsa miR-34b-5p),
      miRBase Accession, MIMAT0000685, HGNC ID No: 31636

<400> SEQUENCE: 1
uaggcagugu cauuagcuga uug                                             23

<210> SEQ ID NO 2
<211> LENGTH: 22
<212> TYPE: RNA
<213> ORGANISM: Artificial Sequence
<220> FEATURE:
<223> OTHER INFORMATION: Mature sequence for miR-34b (hsa miR-34b-3p),
      miRbase Accession No. MIMAT0004676, HGNC ID NO:31636

<400> SEQUENCE: 2
caaucacuaa cuccacugcc au                                              22

<210> SEQ ID NO 3
<211> LENGTH: 23
<212> TYPE: RNA
<213> ORGANISM: Artificial Sequence
<220> FEATURE:
<223> OTHER INFORMATION: Mature sequence for miR-34c (hsa miR-34c-5p),
      miRbase Accession number MIMAT0000686, HGNC ID NO: 31637

<400> SEQUENCE: 3
aggcagugua guuagcugau ugc                                             23

<210> SEQ ID NO 4
<211> LENGTH: 22
<212> TYPE: RNA
<213> ORGANISM: Artificial Sequence
<220> FEATURE:
<223> OTHER INFORMATION: Mature sequence for miR-592, mirBase acession
      number MIMAT0003260, HGNC ID No.: 32848.

<400> SEQUENCE: 4
uugugucaau augcgaugau gu                                              22
```

METHODS OF TREATING EPILEPSY USING NEURAL STEM CELLS THAT EXPRESS NANOG, SSEA-4, OCT-4, MIR-34B, MIR-34C AND MIR-592

CROSS REFERENCE TO RELATED APPLICATIONS

This application is a divisional of now abandoned U.S. patent application Ser. No. 14/043,221, having the title "Neural Cell Compositions and Methods of Use Related to Epilepsy," filed on Oct. 1, 2013, the entirety of which is incorporated by reference. This application claims the priority benefit of U.S. Provisional Patent Application Ser. No. 61/708,244 filed on Oct. 1, 2012, the entirety of which is incorporated by reference.

SEQUENCE LISTING

This application contains a sequence listing filed in electronic form as an ASCII.txt file entitled 02326480.txt, created on Nov. 19, 2014, and having a size of 1460 bytes. The content of the sequence listing is incorporated herein in its entirety.

BACKGROUND OF THE INVENTION

1) Field of the Invention

The field of the invention is epilepsy study and treatment.

2) Description of Related Art

Over three million Americans suffer from some form of epilepsy, with mesial temporal lobe epilepsy (MTLE) being the most common, arising from the temporal lobe structures of amygdala, hippocampus and parahippocampal gyms. While many antiepileptic drugs are available, temporal lobectomy is the definitive treatment for intractable temporal lobe epilepsy.

Although there are in vitro models for the study of epilepsy, most neurological disease models use animal tissues/cells, thus they do not fully recapitulate the human disease pathology. There is therefore a need for a humanized in vitro model for the study of epilepsy. Further, the molecular basis for epileptic pathologies is far from elucidated. Obtaining a better understanding of the disease pathology of various forms of epilepsy such as temporal lobe epilepsy may lead to novel biomarkers and treatments for this disorder.

A microRNA (miRNA) is a small non-coding RNA molecule (ca. 22 nucleotides) found in plants and animals, which functions in transcriptional and post-transcriptional regulation of gene expression. Encoded by eukaryotic nuclear DNA, miRNAs function via base-pairing with complementary sequences within mRNA molecules, usually resulting in gene silencing via translational repression or target degradation. The human genome may encode over 1000 miRNAs, which may target about 60% of mammalian genes and are abundant in many human cell types.

MicroRNAs are well conserved in eukaryotic organisms and are thought to be a vital and evolutionarily ancient component of genetic regulation. Animal miRNAs typically exhibit only partial complementarity to their mRNA targets. A seed region of about 6-8 nucleotides in length at the 5' end of an animal miRNA is thought to be an important determinant of target specificity. Combinatorial regulation is a feature of miRNA regulation. A given miRNA may have multiple different mRNA targets, and a given target might similarly be targeted by multiple miRNAs.

Three such miRNAs are miR-34b (SEQ ID NOs: 1 and 2), miR-34c (SEQ ID NO: 3), and miR-592 (SEQ ID NO: 4). The gene encoding miR-34b is also referred to as MIR34B, microRNA 34b and MIRN34B. One gene encoding miR-34b RNA is identified by the HUGO Gene Nomenclature Committee as HGNC:31636. The gene encoding miR-34c is also referred to as MIR34C, microRNA 34c and MIRN34C. One gene encoding miR-34c RNA is identified by the HUGO Gene Nomenclature Committee as HGNC:31637. The gene encoding miR-592 RNA is also referred to as MIR592, microRNA 592, MIRN592 and hsa-mir-592. One gene encoding miR-592 RNA is identified by the HUGO Gene Nomenclature Committee as HGNC:32848.

BRIEF DESCRIPTION OF THE DRAWINGS

FIG. 2 is a table showing the results of RT-PCR and miRNA array analyses of microRNAs obtained from TLE patients.

FIG. 11 (A-F) provides two brain images showing a kainic acid-induced lesion (A, D), Hoechst staining (B, E), and a merged image (C, F).

FIG. 12 (A-H) provides a brain images showing a kainic acid-induced lesion (A, D, G), Hoechst staining (B, E), and a merged image (C, F, H).

FIG. 13 (A-F) provides two brain images showing a kainic acid-induced lesion (A, D), Hoechst staining (B, E), and a merged image (C, F).

DETAILED DESCRIPTION

Figure 1:
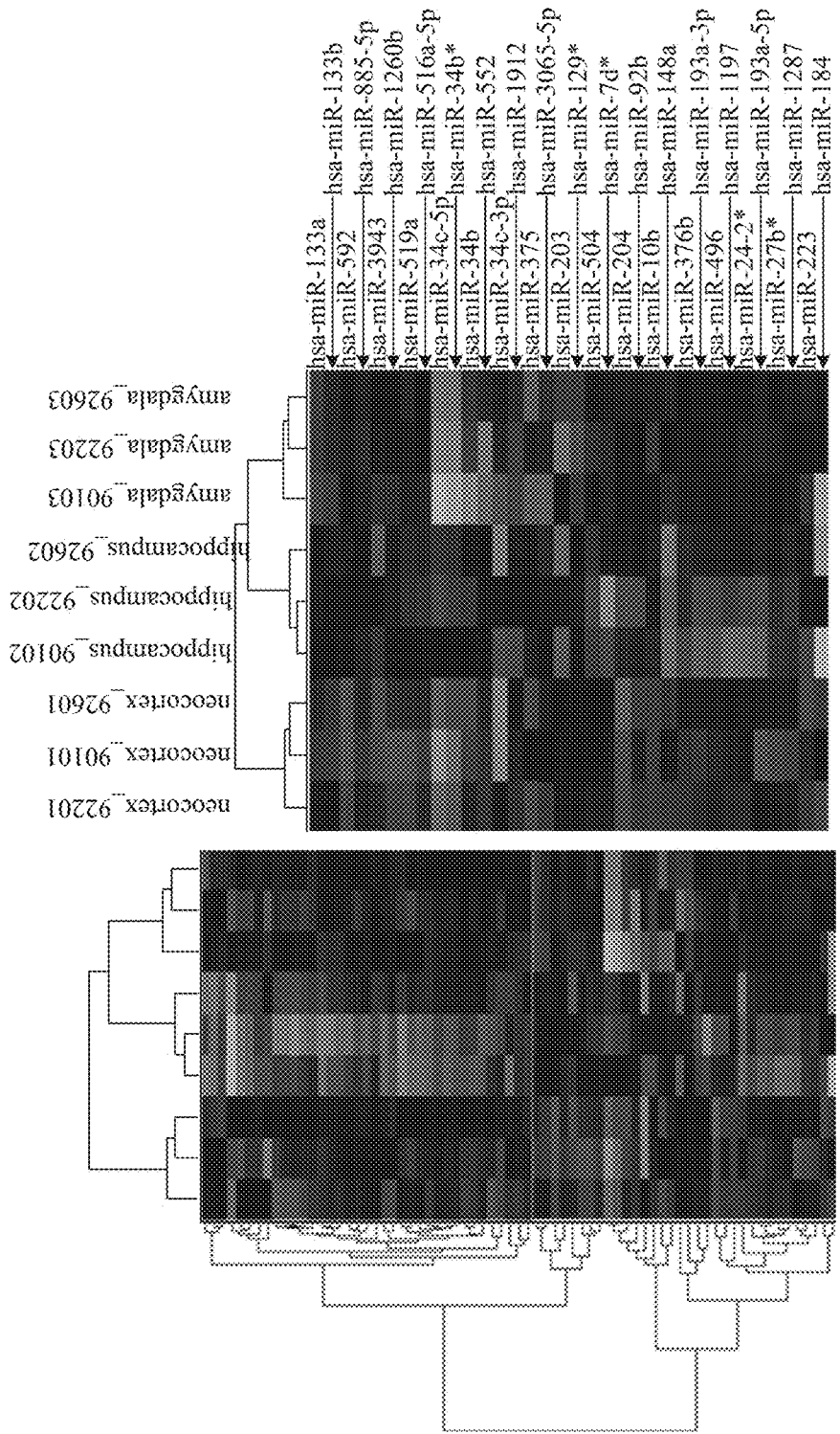
FIG. 1 shows the results of a Gene Cluster analysis of microRNAs obtained from TLE patients.
Figure 3A:
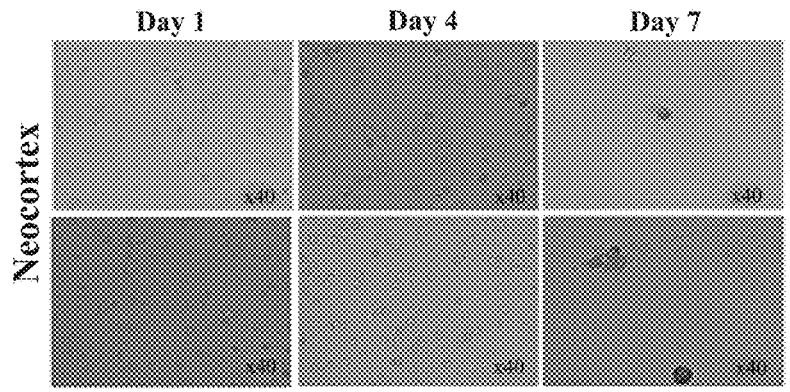
FIG. 3 (A-F) shows the results of culturing cells derived from the neocortex, subventricular zone, entorhinal cortex, hippocampus, amygdala, and dentate gyrus.
Figure 3B:
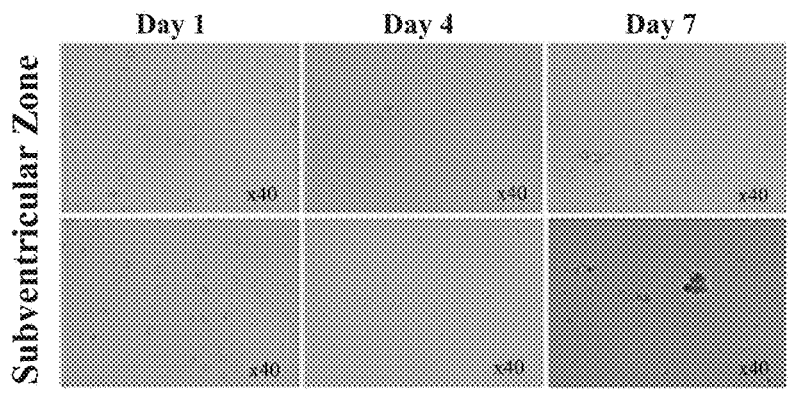
Figure 3C:
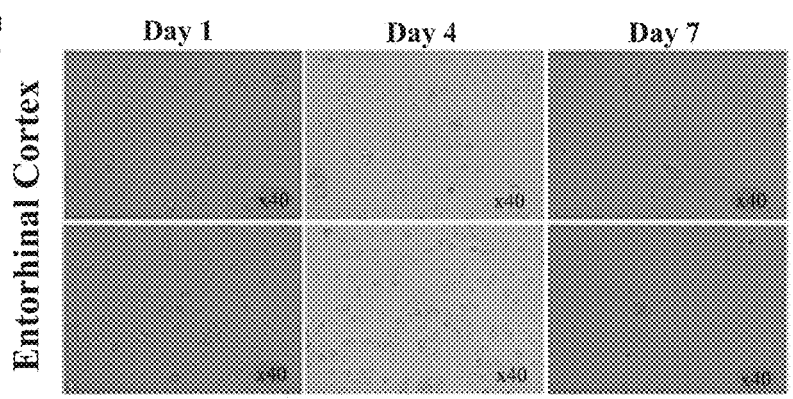
Figure 3D:
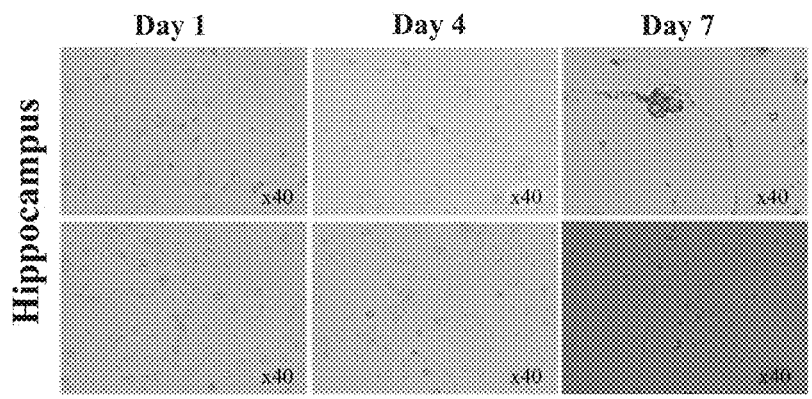
Figure 3E:
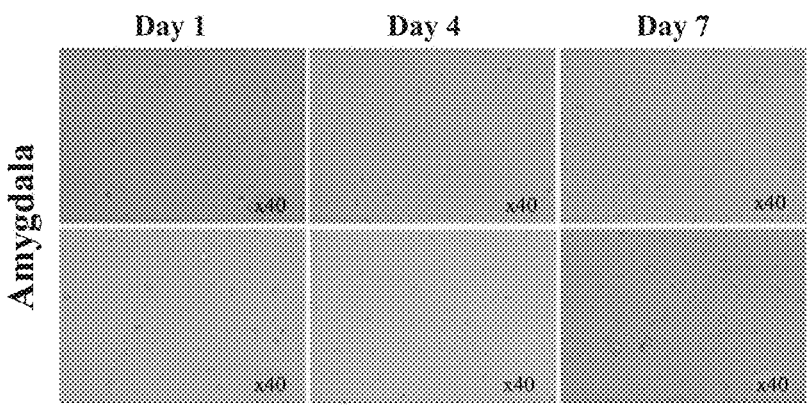
Figure 3F:
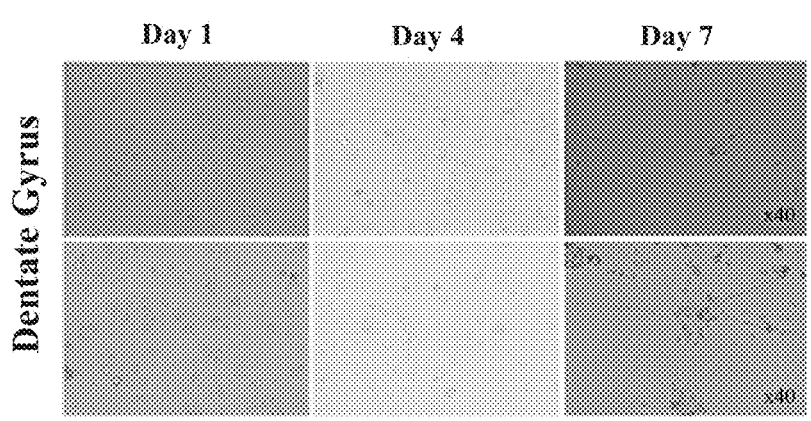
Figure 4A:
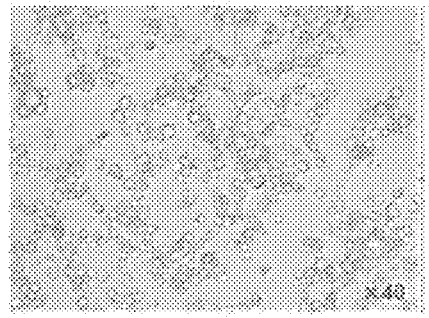
FIG. 4 (A-F) shows the outgrowth processes were short and pruned in cells derived from the hippocampus.
Figure 4D:
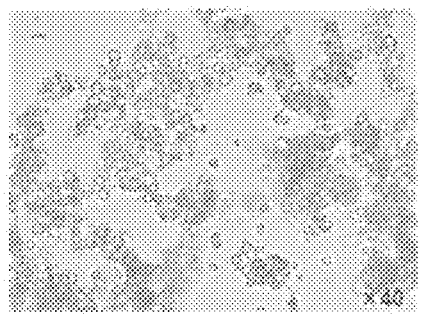
Figure 4B:
Figure 4E:
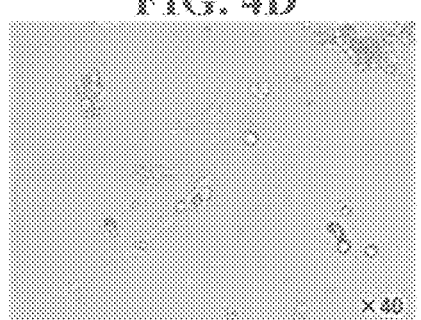
Figure 4C:
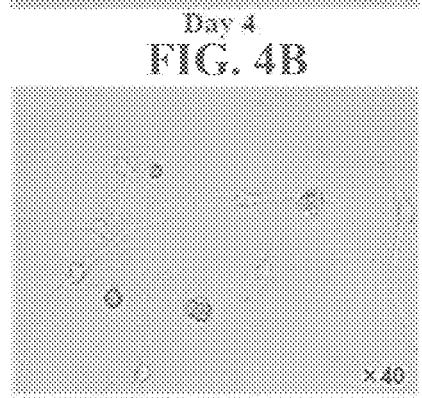
Figure 4F:
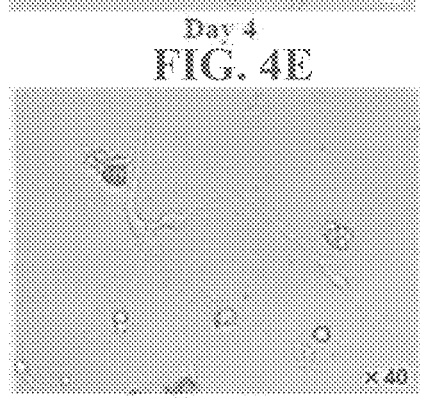
Figure 5A:
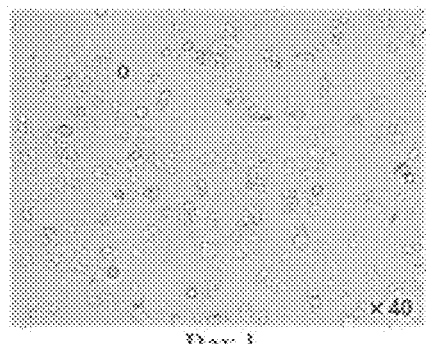
FIG. 5 (A-F) shows the outgrowth processes in cells derived from the amygdala.
Figure 5D:
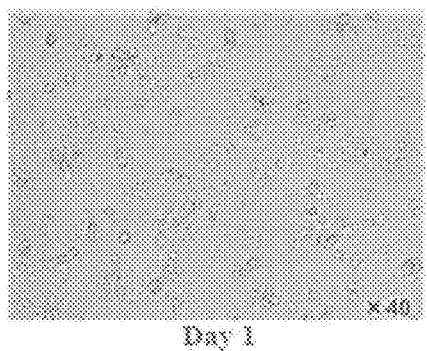
Figure 5B:
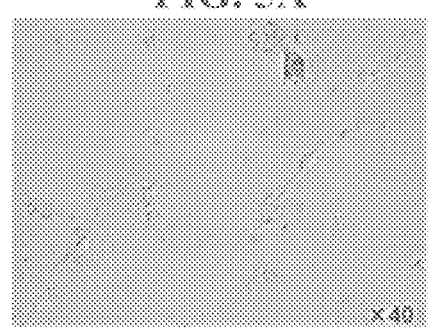
Figure 5E:
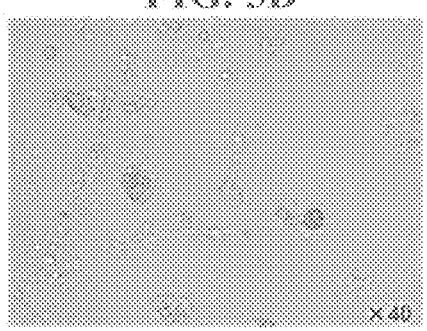
Figure 5C:
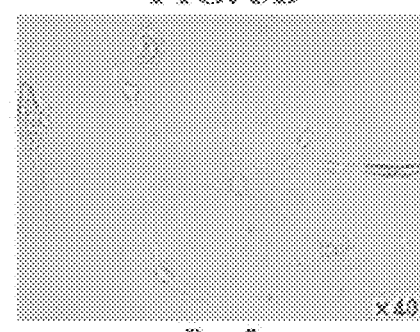
Figure 5F:
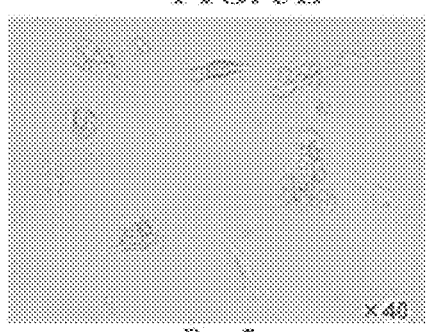
Figure 6A:
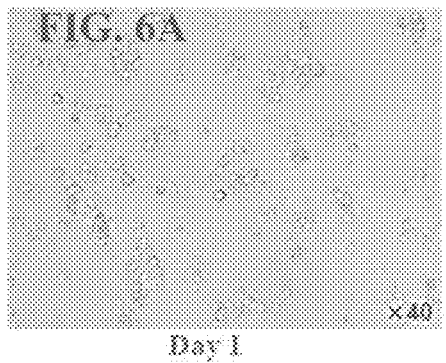
FIG. 6 (A-F) shows the outgrowth processes in cells derived from the cortex.
Figure 6D:
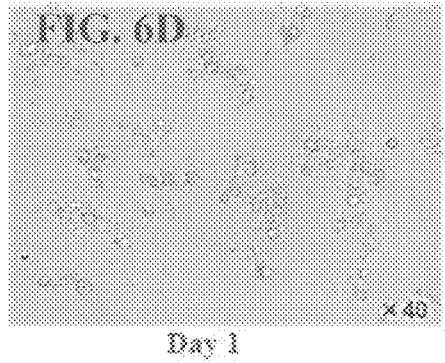
Figure 6B:
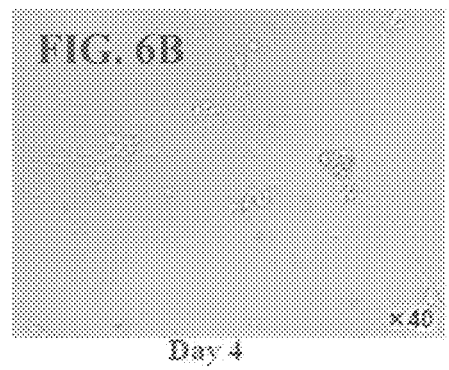
Figure 6E:
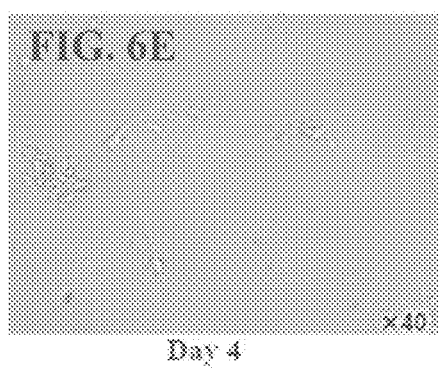
Figure 6C:
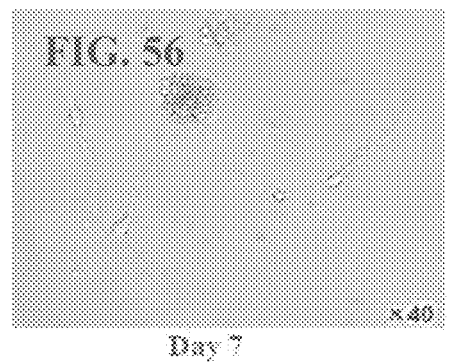
Figure 6F:
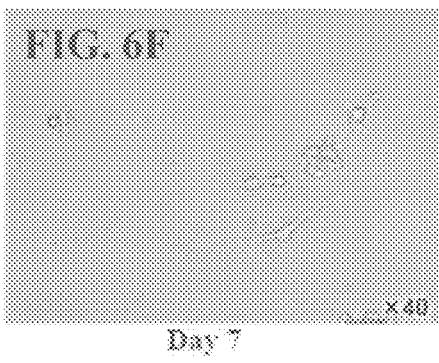

Provided herein is a method of diagnosing or prognosing an epilepsy or epilepsy-related disorder. Also provided herein is a method of treating an epilepsy or epilepsy-related disorder. Further provided are non-epileptic and epileptic neural cells and cell cultures. Term definitions used in the specification and claims are as follows.

DEFINITIONS

As used in the specification and claims, the singular form "a," "an," and "the" include plural references unless the context clearly dictates otherwise. For example, the term "a polynucleotide" includes a plurality of polynucleotides, including mixtures thereof.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The terms "cell line" and "cell culture" refer to a collection of cells that are progeny of an isolated single cell, a multiple cell of a single cell type, or multiple cells from a single cell source that are maintained ex vivo under controlled conditions. In some embodiments, the cell culture is maintained for approximately 2, 3, 4, 5, or more cell passages. It is also understood that all progeny may not be precisely identical in DNA content, due to deliberate or inadvertent mutations. Variant progeny that have the same function or biological property, as screened for in the originally isolated cell(s), are included.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." In some embodiments, a control for an epileptic neural stem cell is a non-epileptic neural stem cell.

The terms "diagnosing," "diagnosis," "prognosing," and "prognosis" refer to one or more actions taken by a physician or other healthcare professional related to the advisement of a patient regarding a particular illness, disorder or condition. It should be understood that these terms require more than a mere mental consideration of the diagnostic or prognostic information obtained through the practice of the present invention.

"Differentially expressed" as applied to a gene refers to the differential production of the mRNA transcribed from the gene or the protein product encoded by the gene. A differentially expressed gene may be over-expressed or under-expressed as compared to the expression level of a normal or control cell. In one aspect, it refers to a differential that is 2.5 times, preferably 5 times, or preferably 10 times higher or lower than the expression level detected in a control sample. The term "differentially expressed" also refers to nucleotide sequences in a cell or tissue which are expressed where silent in a control cell or not expressed where expressed in a control cell.

An "effective amount" is an amount sufficient to effect beneficial or desired results. An effective amount can be administered in one or more administrations, applications or dosages.

The term "epilepsy" refers herein to a diverse set of chronic neurological disorders characterized by seizures. The term "epilepsy" includes, but is not limited to, benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, and photosensitive epilepsy. In some embodiments, the epilepsy treated, prognosed or diagnosed according to the present invention is temporal lobe epilepsy. Temporal lobe epilepsy is a symptomatic localization-related epilepsy and is the most common epilepsy of adults who experience seizures poorly controlled with anticonvulsant medications. In most cases, the epileptogenic region is found in the midline (mesial) temporal structures (e.g., the hippocampus, amygdala, and parahippocampal gyms). Seizures usually begin in late childhood and adolescence. Most of these patients have complex partial seizures sometimes preceded by an aura, and some TLE patients also have secondary generalized tonic-clonic seizures.

As used herein, "expression" refers to the process by which polynucleotides are transcribed into miRNA. If the polynucleotide is derived from genomic DNA, expression may include splicing of the miRNA in a eukaryotic cell. "Over-expression" as applied to a gene refers to the overproduction of the mRNA transcribed from the gene or the protein product encoded by the gene, at a level that is 2.5 times higher, preferably 5 times higher, more preferably 10 times higher than the expression level detected in a control sample. "Under-expression" as applied to a gene refers to the under-production of the mRNA transcribed from the gene or the protein product encoded by the gene, at a level that is 2.5 times lower, preferably 5 times lower, more preferably 10 times lower than the expression level detected in a control sample.

"Mammal" for purposes of treatment refers to any animal classified as a mammal, including human, domestic and farm animals, nonhuman primates, and zoo, sports, or pet animals, such as dogs, horses, cats, cows, etc.

The term "neural stem cell" (also referred to as "NSC") refers herein to a multipotent neural cell that differentiates into one or more nervous system cells including, but not limited to, neuroblasts, glioblasts (including Type 1A or Type 02A), intermediate neural progenitors, projecting neurons, interneurons, astrocytes (including Type 1 and Type 2), and oligodendrocytes. In some embodiments, a neural stem cell expresses, over-expresses, or is considered positive for one or more stem cell identifiers including, but not limited to, GFAP, Nestin, PSA-NCAM, Nanog, SSEA-4, Oct-4, CXCR4, LIF, FGF, EGF, PDGF, and Notch.

As used herein, a "non-epileptic neural stem cell" is a neural stem cell obtained from a region near a hippocampus or in a neocortex region in a subject. In one embodiment, the non-epileptic neural stem cell is isolated using the methods provided in Example 3. In some embodiments, a non-epileptic neural stem cell over-expresses Nanog, SSEA-4 and OCT-4 as compared to a epileptic neural stem cell.

As used herein, an "epileptic neural stem cell" is a neural stem cell having over-expression of a miR-34b polynucleotide sequence and/or a miR-34c polynucleotide sequence and under-expression of a miR-592 polynucleotide sequence as compared to a control, wherein the control is a non-epileptic neural stem cell. In one embodiment, the epileptic neural stem cell is isolated using the methods provided in Example 3. In some embodiments, the epileptic neural stem cell under-expresses Nanog, SSEA-4 and OCT-4 as compared to a non-epileptic neural stem cell.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The term "pharmaceutically acceptable salts" refers to any acid or base addition salt whose counter-ions are non-toxic to the subject to which they are administered in pharmaceutical doses of the salts.

The terms "pharmaceutically effective amount," "therapeutically effective amount" or "therapeutically effective dose" refer to the amount of a compound such as a non-epileptic neural stem cell that will elicit the biological or medical response of a tissue, system, animal, or human that is being sought by the researcher, veterinarian, medical doctor or other clinician.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure and may perform any function, known or unknown. The following are non-limiting examples of polynucleotides: a gene or gene fragment, exons, introns, messenger RNA (mRNA), transfer RNA, ribosomal RNA, microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "subject," "individual" or "patient" is used interchangeably herein, which refers to a vertebrate, preferably a mammal.

The term "therapeutically effective amount" includes that amount of a compound such as a non-epileptic neural stem cell that, when administered, is sufficient to prevent development of, or alleviate to some extent, one or more of the symptoms of the condition or disorder being treated. The therapeutically effective amount will vary depending on the compound such as a non-epileptic neural stem cell, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a non-epileptic neural stem cell includes an amount that is sufficient to treat epilepsy.

The terms "treat," "treating," "treatment" and grammatical variations thereof as used herein include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. In some instances, the terms "treat," "treating," "treatment" and grammatical variations thereof include reducing the number of epileptic seizures experienced by a subject as compared with prior to treatment of the subject or as compared with the incidence of such symptom in a general or study population.

DESCRIPTION

Provided herein is a novel technology for harvesting human neural stem cells (hNSCs) and epileptic neural cells from adult patients undergoing neurosurgical resection procedure, as well as novel applications for research (i.e., humanized animal models) and for clinical applications (i.e., biomarker/diagnostic tools, and autologous and allogeneic transplantation). The present disclosure can be applied to other neurological disorders where a neurosurgical resection, ablation, electrode implantation or similar brain tissue manipulation is indicated.

The present disclosure includes 1) a technology for harvesting (hNSCs) from an epilepsy patient undergoing neurosurgical resection procedures, allowing non-epileptic cells surrounding the epileptic tissue to be harvested and thereafter expanded in vitro for generation of an ample supply of hNSCs; 2) a technology involving said neurosurgical resection procedure that allows harvesting of epileptic tissues/cells which can be used as a biomarker or diagnostic tool; 3) a technology for developing humanized in vitro and in vivo models of epilepsy and related neurological disorders which are created using either the generated hNSCs or the epileptic cells; and 4) a clinical application of using the generated hNSCs as allogeneic and autologous therapeutics (e.g., transplant cell source, pharmacological agent, neural circuit scaffold) for treating epilepsy and related disorders.

Converging evidence from microRNA (miRNA), qPCR and immunocytochemical assays described herein identify novel miRNAs associated with epilepsy. These miRNAs are miR-34b, miR-34-c, and miR-592. Prior to this disclosure, there had been no report of miR34b/c and miR-592 as mitigating the pathology of epilepsy. The finding that a signature transcription profile is distinct to a discrete brain structure of the epilepsy brain is novel and has far-ranging preclinical and clinical applications. First, the novel miR profiles can be used to identify an optimal source of stem cells allowing robust cell culture for laboratory work (e.g., in vitro developmental biology studies and humanized animal models), as well as an ample supply of viable cells for clinical transplantation. Second, the distinct brain structure-specific "sternness" signature indicates the potential of autologous transplantation for epilepsy. Third, such gene profile, either as a single miR or a combination of miRs, can be used as a biomarker (i.e., possibly detected in blood serum) of epilepsy and other related disorders.

Accordingly, provided herein is a method of diagnosing or prognosing an epilepsy or epilepsy-related disorder. Also provided herein is a method of treating an epilepsy or epilepsy-related disorder. Further provided are non-epileptic and epileptic neural stem cells and cell cultures.

The epilepsy diagnosed, prognosed, or treated using the present invention can be any form of epilepsy including, but not limited to, benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, and photosensitive epilepsy. In some embodiments, the epilepsy treated, prognosed, or diagnosed according to the present invention is temporal lobe epilepsy. Temporal lobe epilepsy is a symptomatic localization-related epilepsy and is the most common epilepsy of adults who experience seizures poorly controlled with anticonvulsant medications. In most cases, the epileptogenic region is found in the midline (mesial) temporal structures (e.g., the hippocampus, amygdala, and parahippocampal gyms). Seizures usually begin in late childhood and adolescence. Most of these patients have complex partial seizures sometimes preceded by an aura, and some TLE patients also have secondary generalized tonic-clonic seizures.

In some embodiments, a method of diagnosing or prognosing an epilepsy is provided that comprises obtaining a sample from a subject suspected of having, or being predisposed to develop, epilepsy or an epilepsy-related disorder, detecting expression of one or more miR-34b polynucleotide sequences, and/or one or more miR-34c polynucleotide sequences, and/or one or more miR-592 polynucleotide sequences, comparing the expression to a control, and making the diagnosis or prognosis of the epilepsy or epilepsy-related disorder when 1) the miR-34b polynucleotide sequence and/or miR-34c polynucleotide sequence is over-expressed as compared to a miR-34b polynucleotide and/or miR-34c polynucleotide control, respectively, and/or 2) the miR-592 polynucleotide sequence is under-expressed as compared to a miR-592 polynucleotide control. A subject can be predisposed to develop epilepsy due to genetic or environmental factors. In some embodiments, both miR34b and miR34c polynucleotide sequences are over-expressed as compared to their respective controls. In still other embodiments, both miR34b and miR34c polynucleotide sequences are over-expressed as compared to their respective controls, and the miR592 polynucleotide sequence is under-expressed as compared to its control.

"Over-expression" as applied to a miRNA refers to the over-production of the miRNA transcribed from its gene, at a level that is 2.5 times higher, preferably 5 times higher, more preferably 10 times higher than the expression level detected in a control sample. "Under-expression" as applied to a miRNA refers to the under-production of the miRNA transcribed from its gene, at a level that is 2.5 times lower, preferably 5 times lower, more preferably 10 times lower than the expression level detected in a control sample. The sample that is obtained from the subject is preferably obtained from the hippocampus or amygdala region of the subject's brain. A control sample is preferably obtained or derived from a non-epileptic region of a brain including, but not limited to, a region surrounding a hippocampus and a neocortex region. In one embodiment, the control sample is a non-epileptic neural cell as described herein.

It should be understood that the terms "miR-34b," "miR-34c," and "miR-592" refer to any and all polynucleotide sequences having substantial homology with known miR-34b, miR-34c, and miR-592 polynucleotide sequences such that those of skill in the art understand the polynucleotide sequences to be homologs or orthologs of the miR-34b (SEQ ID NOs: 1 and 2), miR-34c (SEQ ID NO: 3), and miR-592 (SEQ ID NO: 4) sequences described herein. One gene encoding miR-34b RNA is identified by the HUGO Gene Nomenclature Committee as HGNC:31636. One gene encoding miR-34c RNA is identified by the HUGO Gene Nomenclature Committee as HGNC:31637. One gene encoding miR-592 RNA is identified by the HUGO Gene Nomenclature Committee as HGNC:32848.

Also provided herein is a method of treating an epilepsy or epilepsy-related disorder in a subject in need of such treatment, comprising administering a non-epileptic neural stem cell to the amygdala or hippocampus region of the subject's brain. As used herein, a "non-epileptic neural stem cell" is a neural stem cell obtained from a region near a hippocampus or in a neocortex region of a subject as further defined above and in the Examples below. The subject can be the same individual that receives the treatment (autologous administration) or a different individual (heterologous administration). The non-epileptic neural stem cell can be administered via any method known to those of skill in the art. In some embodiments, the non-epileptic neural stem cell is administered to the subject via transplantation into an amygdala or hippocampus region of the subject's brain. Accordingly, the non-epileptic neural stem cells can be administered as a transplant material (i.e., allogeneic transplantation) or as a pharmacologic therapeutic (i.e., autologous cell therapy or autologous pharmacologic treatment).

In addition to the methods described above, further provided herein are compositions comprising isolated epileptic neural stem cells and cell lines and isolated non-epileptic stem cells and cell lines. Accordingly, provided herein is a composition comprising an epileptic neural stem cell line, wherein the cell line is derived from an amygdala or hippocampus region of a brain and a characteristic of the cell line is 1) over-expression of a miR-34b polynucleotide sequence and/or a miR-34c polynucleotide sequence as compared to a control and/or 2) under-expression of a miR-592 polynucleotide sequence as compared to a control. In some embodiments, the epileptic neural stem cell line is further characterized by under-expression of Nanog, SSEA-4 and OCT-4 as compared to the control. In one embodiment, the control is a non-epileptic neural cell line.

The examples below describe that isolated epileptic neural stem cells obtained from the amygdala or hippocampus of patients having temporal lobe epilepsy exhibit increased levels of miR-34b RNA sequence and/or a miR-34c RNA sequence and decreased levels of miR-592 RNA sequence as compared to control neural cells. Isolated epileptic neural stem cells having these characteristics are useful in the diagnosis and/or prognosis of epilepsy or an epilepsy-related disorder and for the development of scaffolds and assays for the study of epilepsy or an epilepsy-related disorder. To date, many of the epileptic tissues collected from patients are relegated to research purposes since the tissues/cells come from post-mortem sources. In contrast, the present disclosure describes the harvest of diseased brain cells from an adult human that closely recapitulate the disease pathology, allowing an in-depth examination and a much better understanding of the human disease.

Also provided herein is a composition comprising a non-epileptic neural stem cell line, wherein the cell line is 1) under-expression of a miR-34b polynucleotide sequence and/or a miR-34c polynucleotide sequence as compared to a control and/or 2) over-expression of a miR-592 polynucleotide sequence as compared to an epileptic cell control. In some embodiments, the non-epileptic neural stem cell line is further characterized by over-expression of Nanog, SSEA-4 and OCT-4 as compared to the control. In other or further embodiments, the non-epileptic neural stem cell line is characterized by increased production of one or more of a brain-derived neurotrophic factor (BDNF), a glial cell line-derived neurotrophic factor (GDNF), and a nerve growth factor (NGF) as compared to a epileptic neural stem cell line. The non-epileptic neural stem cell line can be derived from a neocortex or hippocampal region of a brain, and in some embodiments, is created using methods equivalent to those provided in Example 3 below.

The examples below further describe that isolated non-epileptic neural stem cells obtained from the neocortex of patients having temporal lobe epilepsy exhibited decreased levels of miR-34b RNA sequence and/or a miR-34c RNA sequences and increased levels of miR-592 RNA sequences as compared to control neural cells. Isolated neural cells having these characteristics are useful as a source of multipotent neural cells that may be used for transplantation, treatment of epilepsy or epilepsy-related disorders and the development of cell lines, scaffolds and assays.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

Pursuant to necessary regulatory approval, tissues from multiple brain regions were obtained from consenting TLE patients undergoing hippocampal resection. Specimens were processed for microRNA. Approximately 800 microRNAs were examined. Results revealed that miR-34b and miR-34c were significantly up-regulated in hippocampus and amygdala compared to the neocortex, with miR-34b/c expression highest in the amygdala. In contrast, levels of miR-592 were significantly down-regulated in the hippocampus and amygdala compared to the neocortex. See FIG. 1. The following notations apply to FIG. 1:
1. Load 71 significant (FDR<0.05), log 2 transformed probes into Gene Cluster 3.0
2. Adjusted data by centering genes (median)
3. Performed clustering using centered correlation as distance measure and average linkage as method Example 2

Sister brain tissues of profiled microRNA samples were then processed for RT-PCR focusing on the identified novel miRs. RT-PCR data generally support microRNA data. Notably, levels of miR-34b/c were significantly up regulated, while levels of miR-592 were down regulated in the hippocampus and amygdala compared to neocortex. FIG. 2 provides a summary of this data.

Example 3

Both non-epileptic and epileptic stem cells were isolated from the TLE samples obtained according to Example 1. More specifically, the epileptic tissue samples (obtained from both the hippocampus/amygdala and neocortex areas) were shipped to the laboratory on frozen brick ice to assure shipment of cells at a cool temperature. The epileptic tissues were treated with 25% trypsin and mechanically dissociated using Pasteur pipets. An average collection was approximately 30 million cells with 30% of adherent cells. Only 1 million cells were required for the first cell culture to select the adherent cells with generally about 30% of the cells demonstrating adherence and about 300,000 cells sub-cultured. The cells doubled approximately every 24 hours. The adherent cells were collected in a buffered saline conical collection tube and subjected to centrifugation at 2,000 rpm for 7 minutes at approximately 4° C. Pelleted cells were resuspended for a cell count and viability test.

The cells were grown to 3 passages before testing without observing signs of contamination. One milliliter of cellular suspension was tested for the total cell count, cell viability, and immunocytochemical analysis for specific markers. The remainder of the cell suspension was used as the NSC product for immunocytochemical assay and transplantation experiments. Alternatively, the cell suspension was cryopreserved in a total volume of 10 mL comprising of 5 mL of cells, 3 mL of the buffered saline (DPBS), 1 mL of the protein HSA (Telacris Bio, Clayton, N.C.), and 1 mL of the preservative DMSO (99% Stemsol). Cryovials were transferred to a cryogenic storage unit and stored in the vapor phase of liquid nitrogen at a temperature at or below −150° C. (LN2 Freezer MVE 1830; Chart Industries, Garfield Heights, Ohio).

FIG. 3 (A-F) shows that stem cell culture was poor when cells were harvested from the amygdala of human epileptic patients, which was shown to display a significant increment in miR-34b/c and a significant decrement in miR-592. Conversely, stem cell culture was robust when cells were harvested from the neocortex of human epileptic patients, which was shown to display a significant decrement in miR-34b/c and a significant increment in miR-592.

Example 4

Cells were isolated from the TLE samples obtained according to Example 1 and immunocytochemical staining against stem cell markers and cell survival/death markers was performed. These assays provided insights into the function of miR-34b/c and miR-592, in that distinct growth and proliferation patterns were recognized from stem cells harvested from hippocampus, amygdala and neocortex. Stem cells derived from the hippocampus, amygdala, and cortex of a TLE patient were stained with Hoechst stain (identifies DNA), GFAP (glial fibrillary acidic protein), Nestin, Nanog (a transcription factor associated with an undifferentiated state), SSEA-4, and Oct-4 (data not shown).

Taken together, these immunocytochemical staining results reveal the following:
1. Double-positive cells expressing astrocytic cell marker GFAP and immature neural cell marker Nestin were detected in all brain tissue sources.
2. The stem cell markers Nanog, SSEA-4 and Oct-4 are also expressed on cells obtained from all three brain tissue sources.
3. Apoptotic cell death marker p53 staining intensity is generally weak, but the other apoptotic cell death marker Caspase-3 intensity is strong and Caspase-3 positive cells are visible in all brain tissue sources.
4. While neural differentiation, cell proliferation (i.e., stem cell phenotype), and apoptotic markers are detected in all brain tissue sources, there is a tendency of enhancement and reduction in their expression that coincides with miR-34 and miR-592 up-regulation and down-regulation in specific brain tissues examined.

In summary, this data shows that expression of stem cell markers Nanog, SSEA-4 and OCT-4 is detected, but modestly in the core epileptic brain region of hippocampus and the immediate adjacent brain area of amygdala. In contrast, these stem cell markers are robustly expressed in the cortex, a distant brain area from the epileptic tissue. Note that the expression of miR-34 and miR-592 are inversely expressed in hippocampus and amygdala versus the cortex (See FIG. 7), providing direct role of these miRs in stem cell fate.

Similarly, expression of the apoptotic marker caspase-3, but not p53, is increased in hippocampus and amygdala, but only modestly detected in cortex, suggesting that epileptic core and adjacent brain areas of hippocampus and amygdala are susceptible to apoptotic cell death, but the non-epileptic cortex appears resistant to this cell death process. Moreover, the direct role of miR-34 and miR-592 in cell death is demonstrated here.

The neural differentiation markers, GFAP and Nestin, revealed a similar level of expression across all brain tissue sources examined, but more elaborate and decorated outgrowth processes were recognized in the cells harvested from the cortex (FIG. 6) and partially displayed by those isolated from the amygdala (FIG. 5), whereas these processes were short and pruned in cells derived from the hippocampus (FIG. 4), suggesting that neural differentiation potential is more rampant in the non-epileptic tissue of the cortex compared to the epileptic tissue of hippocampus and its adjacent tissue of amygdala. Moreover, miR-34 and miR-592 also appear to influence the lineage commitment of the cells towards neural differentiation. These results suggest that cell proliferation and differentiation is lower in the hippocampus and amygdala of temporal lobe epileptic patients compared to the neocortex.

Figures 7, 8:
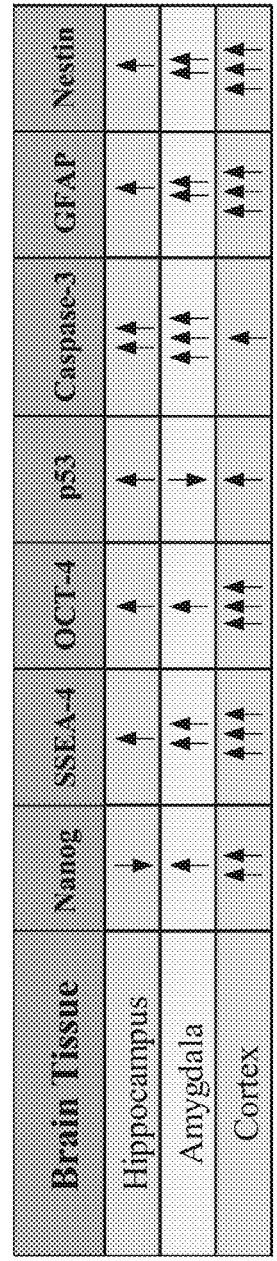
FIG. 7 is a table showing expression of miR-34 and miR-592 in hippocampus, amygdala and cortex tissues.
FIG. 8 is a table showing expression of Nanog, SSEA-4, p53, OCT-4, Caspase-3, GFAP, and Nestin in hippocampus, amygdala and cortex tissues.
Figure 9A:
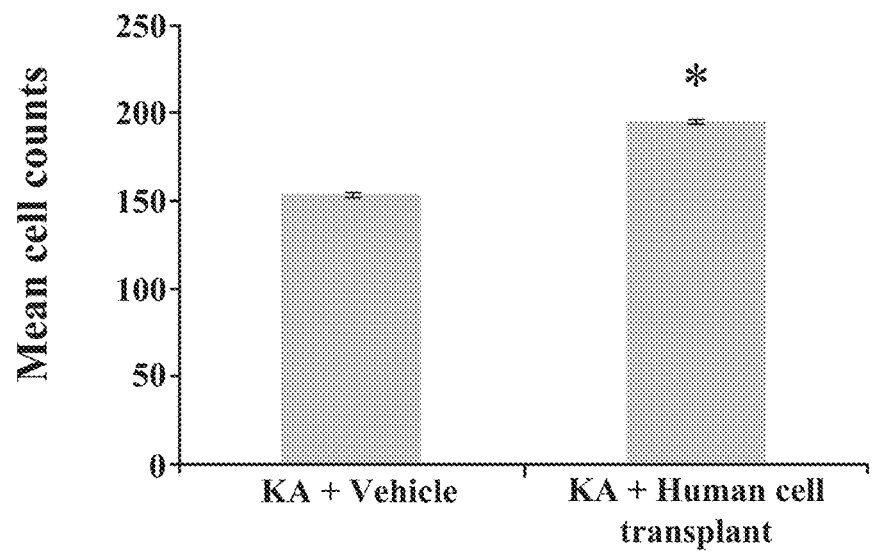
FIG. 9 (A-B) contains graphs showing the mean cell count of stem cells derived from the neocortex (i.e., reduced miR-34b/c but elevated miR-592 expression) that were transplanted into the amygdala.
Figure 9B:
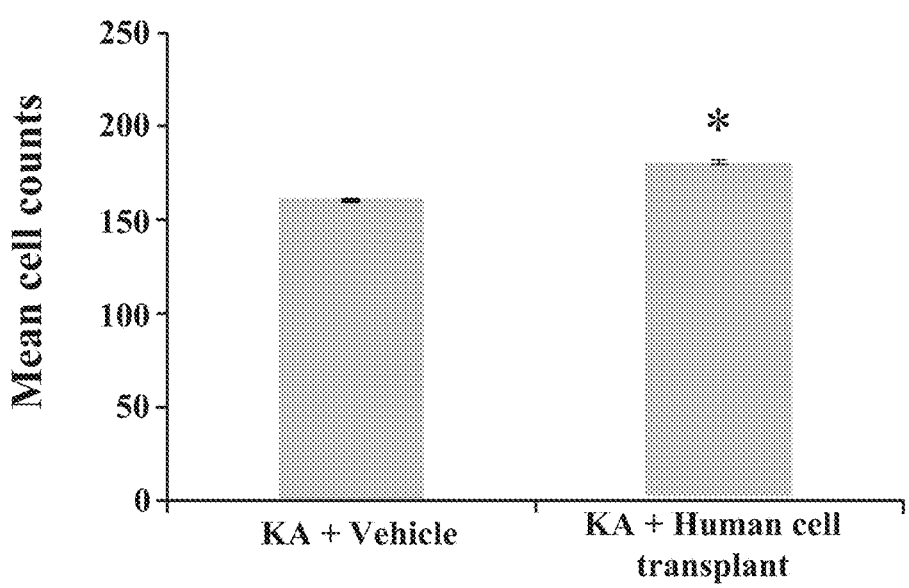
Figure 10A:
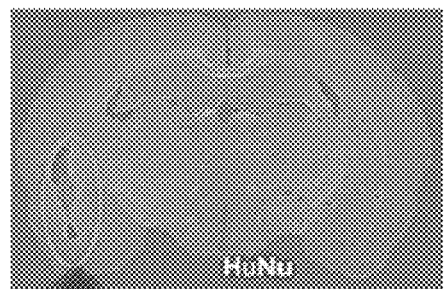
FIG. 10 (A-C) provides a brain image showing a kainic acid-induced lesion (A), Hoechst staining (B), and a merged image (C).
Figures 10B, 10C:
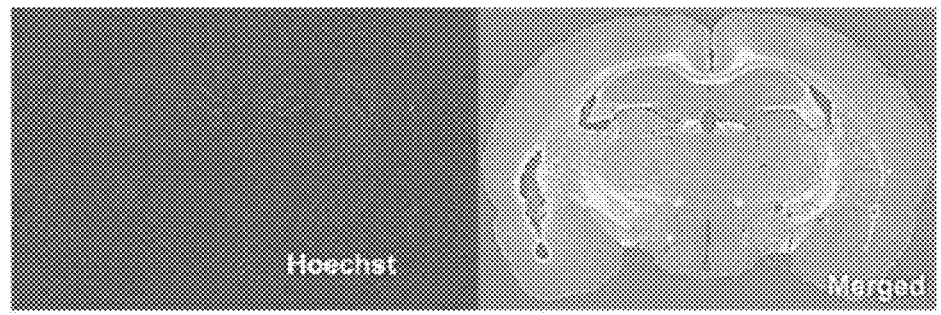
Figure 14A:
FIG. 14 (A-I) provides three brain images showing a kainic acid-induced lesion (A, D, G), Hoechst staining (B, E, H), and a merged image (C, F, I).
Figure 14B:
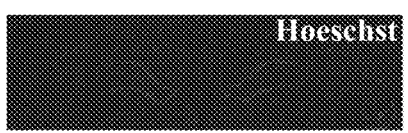
Figure 14C:
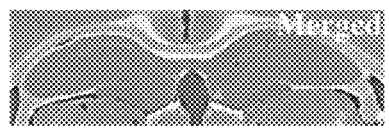
Figure 14D:
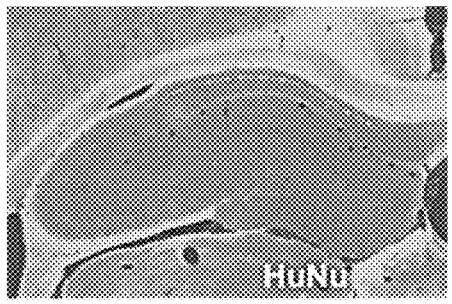
Figure 14E:
Figure 14F:
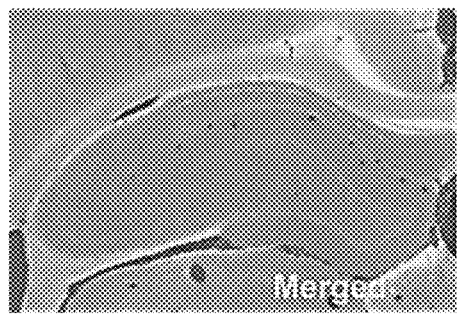
Figure 14G:
Figure 14H:
Figure 14I:
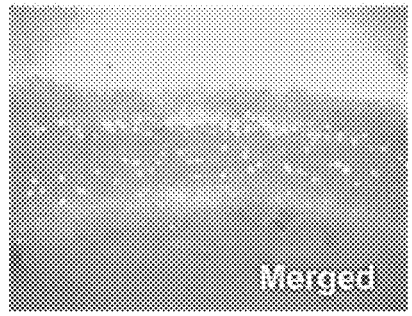
Figure 15B:
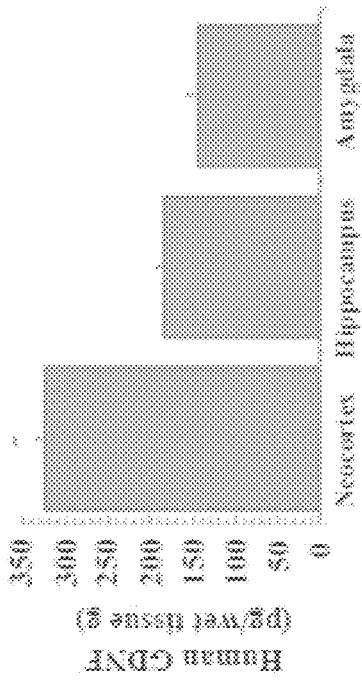
FIG. 15 (A-D) shows the results of ELISA detection of BDNF, GDNF, NGF-beta, and FGF-beta in supernatants of cells derived from the neocortex, amygdala, and hippocampus.
Figure 15D:
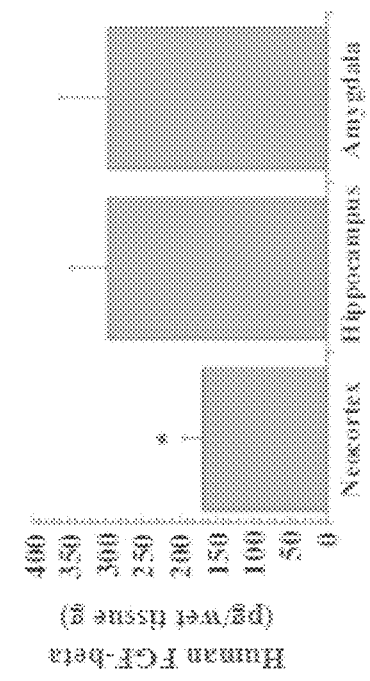
Figure 15A:
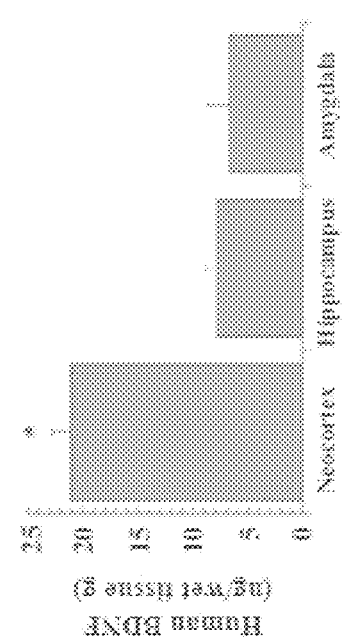
Figure 15C:
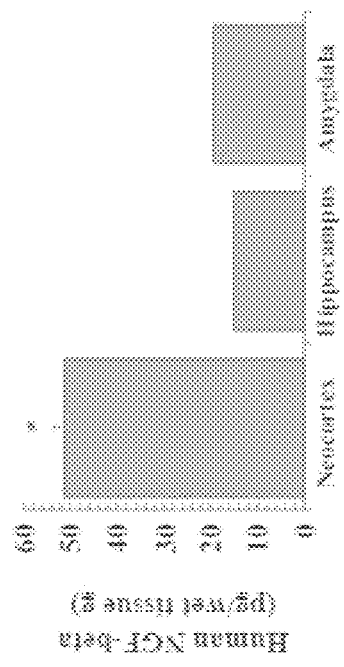

The table in FIG. 8 summarizes the data described above, clarifies the concurrence of the immunocytochemical results with the miR data, and reveals the role of miR-34 and miR-592 in stem cell fate. The table shows that expression of stem cell markers Nanog, SSEA-4 and OCT-4 is detected, but modestly in the core epileptic brain region of hippocampus and the immediate adjacent brain area of amygdala. In contrast, these stem cell markers are robustly expressed in the cortex, a distant brain area from the epileptic tissue. Note that the expression of miR-34 and miR-592 are inversely expressed in hippocampus and amygdala versus the cortex, providing direct role of these miRs in stem cell fate.

Similarly, expression of the apoptotic marker caspase-3, but not p53, is increased in hippocampus and amygdala, but only modestly detected in cortex, suggesting that epileptic core and adjacent brain areas of hippocampus and amygdala are susceptible to apoptotic cell death, but the non-epileptic cortex appears resistant to this cell death process. Moreover, the direct role of miR-34 and miR-592 in cell death is demonstrated here.

The neural differentiation markers, GFAP and Nestin, revealed a similar level of expression across all brain tissue sources examined, but more elaborate and decorated outgrowth processes were recognized in the cells harvested from the cortex and partially displayed by those isolated from the amygdala, whereas these processes were short and pruned in cells derived from the hippocampus, suggesting that neural differentiation potential is more rampant in the non-epileptic tissue of the cortex compared to the epileptic tissue of hippocampus and its adjacent tissue of amygdala. Moreover, miR-34 and miR-592 also appear to influence the lineage commitment of the cells towards neural differentiation.

The table in FIG. 8 indicates how the present disclosure guides the appropriate brain location to harvest transplantable stem cells for treatment of epilepsy and related disorders.

Example 5

To further elucidate the effects of miR-34b/c and miR-592, Sprague-Dawley rats with kainic acid-induced epilepsy received intrahippocampal transplants of brain region-specific tissues from epileptic patients. Animals were first subjected to kainic acid lesion to induce epilepsy (Rao M S, Hattiangady B, Reddy D S, Shetty A K. Hippocampal neurodegeneration, spontaneous seizures, and mossy fiber sprouting in the F344 rat model of temporal lobe epilepsy. J. Neurosci Res 2006 May 1; 83(6):1088-105). Next, animals showing the typical epileptic seizures (stage V) received either transplants of the human cortical cells isolated according to Example 1 or a vehicle infusion around 5 months after KA lesion. One week after transplantation or vehicle infusion, animals were killed for immunohistochemical analyses to reveal rescue of hippocampal cells from KA lesion and also to detect survival of transplanted human cortical cells.

Results are shown in FIGS. 9-14. It was observed that transplantation of stem cells derived from the neocortex (i.e., reduced miR-34b/c but elevated miR-592 expression) not only survived in the amygdala but also reduced the KA-induced hippocampal cell loss in epileptic rats. Moreover, the transplanted human neocortical cells migrated from the amygdala to the lesioned hippocampus, specifically the CA1 and CA3 regions. This transplant study elucidates the key role of microRNAs in the disease pathology of epilepsy and their utility as a stem cell optimization tool for identifying efficacious stem cells for transplantation therapy.

Example 6

Parallel in vitro studies revealed that the administration of the supernatant from cultured human epileptic neocortical stem cells significantly reduced the kainic acid-induced cell death in primary human hippocampal cells compared to control treatments, suggesting that the rescue of the epileptic hippocampus by the transplanted stem cells likely involves a trophic factor mechanism. (Data not shown.)

The supernatant collected over the last 2 days of passage 3 were used for ELISA. The levels of BDNF, GDNF, NGF and FGF were determined using ELISA kits according to the protocols of the manufacturer (BDNF and GDNF from Promega; NGF and FGF from R&D Systems). As shown in FIG. 15, ELISA revealed that brain-derived neurotrophic factor (BDNF), glial cell line-derived neurotrophic factor (GDNF), and nerve growth factor (NGF) were significantly down regulated in the human hippocampus and amygdala compared to the neocortex, while basic fibroblast growth factor (bFGF) was significantly unregulated in the hippocampus and amygdala compared to the neocortex.

The invention claimed is:

1. A method of treating an epilepsy in a subject in need thereof, the method comprising: administering a therapeutically effective amount of a first population of neural stem cells to an amygdala or hippocampus region of the subject's brain, wherein the first population of neural stem cells expresses a microRNA 34b (miR-34b) having a sequence consisting essentially of the nucleic acid sequence of SEQ ID NOs: 1 or 2, a microRNA 34c (miR-34c) having a sequence consisting essentially of the nucleic acid sequence of SEQ ID NO: 3, and a microRNA 592 (miR-592) having a sequence consisting essentially of the nucleic acid sequence of SEQ ID NO: 4, wherein the first population of neural stem cells under-expresses the miR-34b and the miR-34c by at least 2.5 times as compared to a second population of neural stem cells, and over-expresses the miR-592 by at least 2.5 times as compared to the second population of neural stem cells;

wherein the first population of neural stem cells is generated by
isolating the first population of cells from the neocortex of the subject's brain or an allogenic brain of a non-epileptic subject or an epileptic subject;
culturing the isolated first population of cells;
obtaining the adherent cells after culturing;
expanding the adherent cells by culturing the adherent cells for at least three passages to produce expanded adherent cells; and
identifying the first population of neural stem cells by measuring the expression of the Nanog homeobox protein (Nanog), the stage-specific embryonic antigen-4 protein (SSEA-4), the octamer-binding transcription factor 4 protein (OCT-4), the miR-34b, the miR-34c and the miR-592 in the expanded adherent cells cultured from the first population of cells, wherein the first population of neural stem cells expresses the Nanoq, the SSEA-4, the OCT4, the miR-34b, the miR-34c and the miR-592; and wherein the second population of neural stem cells is generated by
isolating the second population of cells from the amygdala or the hippocampus of the subject's brain or an allogenic brain of an epileptic subject;
culturing the isolated second population of cells;
obtaining the adherent cells after culturing;
expanding the adherent cells by passaging the adherent cells for at least three passages to produce expanded adherent cells; and
identifying the second population of neural stem cells by measuring the expression of the Nanoq, the SSEA-4, the OCT-4, the miR-34b, the miR-34c and the miR-592 in the expanded adherent cells cultured from the second population of cells, wherein the second-population of neural stem cells expresses the Nanoq, the SSEA-4, the OCT-4, the miR-34b, the miR-34c and the miR-592; and wherein the first population of neural stem cells over-expresses the Nanoq, the SSEA-4, and the OCT-4 as compared to the second population of neural stem cells, and wherein the first population of neural stem cells under-expresses the miR-34b and the miR-34c by at least 2.5 times as compared to a second population of neural stem cells, and over-expresses the miR-592 by at least 2.5 times as compared to the second population of neural stem cells.

2. The method of claim 1, wherein the first population of neural stem cells is administered to the subject's brain via transplantation.

3. The method of claim 1, wherein the first population of neural stem cells is administered to the amygdala region of the subject's brain.

4. The method of claim 1, wherein expression of the Nanog, the SSEA-4, and the OCT-4 proteins is measured using immunodetection using antibodies that can specifically bind the Nanog, the SSEA-4, and the OCT-4.

5. The method of claim 1, wherein the first population of cells is isolated from the neocortex of the subject's brain.

6. The method of claim 5, wherein the second population of cells is isolated from the amygdala or hippocampus of the allogenic brain from an epileptic subject.

7. The method of claim 5, wherein the second population of cells is isolated from the amygdala or hippocampus of the subject's brain.

8. The method of claim 1, wherein the first population of cells is isolated from the neocortex of the allogenic brain of an epileptic subject.

9. The method of claim 8, wherein the second population of cells is isolated from the amygdala or hippocampus of the subject's brain.

10. The method of claim 8, wherein the second population of cells is isolated from the amygdala or hippocampus of the allogenic brain of an epileptic subject.

11. The method of claim 1, wherein the first population of cells is isolated from the neocortex of the allogenic brain of a non-epileptic subject.

12. The method of claim 11, wherein the second population of cells is isolated from the amygdala or hippocampus of the subject's brain.

13. The method of claim 11, wherein the second population of cells is isolated from the amygdala or hippocampus of the allogenic brain of an epileptic subject.

14. A method of treating temporal lobe epilepsy in a subject in need thereof, the method comprising: administering a therapeutically effective amount of a first population of neural stem cells to an amygdala or hippocampus region of the subject's brain, wherein the first population of neural stem cells expresses a microRNA 34b (miR-34b) having a sequence consisting essentially of the nucleic acid sequence of SEQ ID NOs: 1 or 2, a microRNA 34c (miR-34c) having a sequence consisting essentially of the nucleic acid sequence of SEQ ID NO: 3, and a microRNA 592 (miR-592) having a sequence consisting essentially of the nucleic acid sequence of SEQ ID NO: 4, wherein the first population of neural stem cells under-expresses the miR-34b and the miR-34c by at least 2.5 times as compared to a second population of neural stem cells, and over-expresses the miR-592 by at least 2.5 times as compared to the second population of neural stem cells;

wherein the first population of neural stem cells is generated by
isolating the first population of cells from the neocortex of the subject's brain or an allogenic brain of a temporal lobe epileptic subject;
culturing the isolated first population of cells;
obtaining the adherent cells after culturing;
expanding the adherent cells by culturing the adherent cells for at least three passages to produce expanded adherent cells; and
identifying the first population of neural stem cells by measuring the expression of the Nanog homeobox protein (Nanog), the stage-specific embryonic antigen-4 protein (SSEA-4), the octamer-binding transcription factor 4 protein (OCT-4), the miR-34b, the miR-34c and the miR-592 in the expanded adherent cells cultured from the first population of cells, wherein the first population of neural stem cells express the Nanoq, the SSEA-4, the OCT-4, the miR-34b, the miR-34c and the miR-592; and wherein the second population of neural stem cells is generated by isolating the second population of cells from the amygdala or the hippocampus of the subject's brain or an allogenic brain of a temporal lobe epileptic subject;

culturing the isolated second population of cells;

obtaining the adherent cells after culturing;

expanding the adherent cells by culturing the adherent cells for at least three passages to produce expanded adherent cells; and identifying the second population of neural stem cells by measuring the expression of the Nanoq, the SSEA-4, the OCT-4, the miR-34b, the miR-34c and the miR-592 in the expanded adherent cells cultured from the second population of cells, wherein the second population of neural stem cells expresses the Nanoq, the SSEA-4, the OCT-4, the miR-34b, the miR-34c and the miR-592; and wherein the first population of neural stem cells over-expresses the Nanoq, the SSEA-4, and the OCT-4 as compared to the second population of neural stem cells, and wherein the first population of neural stem cells under-expresses the miR-34b and the miR-34c by at least 2.5 times as compared to a second population of neural stem cells, and over-expresses the miR-592 by at least 2.5 times as compared to the second population of neural stem cells.

\* \* \* \* \*